(12) United States Patent
Jang

(10) Patent No.: US 12,138,020 B2
(45) Date of Patent: *Nov. 12, 2024

(54) APPARATUS AND METHOD FOR DETECTING BIO-SIGNAL FEATURE

(71) Applicant: SAMSUNG ELECTRONICS CO., LTD., Suwon-si (KR)

(72) Inventor: Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,847

(22) Filed: Jan. 9, 2023

(65) Prior Publication Data

US 2023/0157554 A1  May 25, 2023

Related U.S. Application Data

(62) Division of application No. 16/044,020, filed on Jul. 24, 2018, now Pat. No. 11,576,584.

(30) Foreign Application Priority Data

Jul. 25, 2017 (KR) .................. 10-2017-0094310

(51) Int. Cl.
A61B 5/021 (2006.01)
A61B 5/00 (2006.01)
A61B 5/024 (2006.01)

(52) U.S. Cl.
CPC ...... A61B 5/02116 (2013.01); A61B 5/02108 (2013.01); A61B 5/02416 (2013.01);
(Continued)

(58) Field of Classification Search
CPC ............ A61B 5/02116; A61B 5/02108; A61B 5/02416; A61B 5/7203; A61B 5/7235;
(Continued)

(56) References Cited

U.S. PATENT DOCUMENTS 6,463,311 B1 * 10/2002 Diab .................. A61B 5/14551
600/336
8,652,055 B2 2/2014 Saitou
(Continued)

FOREIGN PATENT DOCUMENTS

JP 2007-135678 A 6/2007
JP 2016-220886 A 12/2016
(Continued)

OTHER PUBLICATIONS

Slapniar G, Mlakar N, Lutrek M. Blood Pressure Estimation from Photoplethysmogram Using a Spectro-Temporal Deep Neural Network. Sensors (Basel). Aug. 4, 2019;19(15):3420. doi: 10.3390/s19153420. PMID: 31382703; PMCID: PMC6696196. (Year: 2019).*
(Continued)

Primary Examiner — Yi-Shan Yang
Assistant Examiner — Kyle W. Kretzer
(74) Attorney, Agent, or Firm — Sughrue Mion, PLLC

(57) ABSTRACT

An apparatus and method for detecting a bio-signal feature are provided. The apparatus according to one aspect may include: a bio-signal acquirer configured to acquire a bio-signal; and a processor configured to generate an envelope signal of the bio-signal, and detect at least one feature of the bio-signal based on a difference between the envelope signal and the bio-signal.

10 Claims, 15 Drawing Sheets

(52) U.S. Cl.
CPC .......... *A61B 5/7203* (2013.01); *A61B 5/7235* (2013.01); *A61B 5/7239* (2013.01); *A61B 5/7278* (2013.01); *G06F 2218/06* (2023.01); *G06F 2218/10* (2023.01)

(58) Field of Classification Search
CPC ... A61B 5/7242; A61B 5/7239; A61B 5/7278; G06F 2218/06; G06F 2218/10
See application file for complete search history.

(56) References Cited

U.S. PATENT DOCUMENTS

| | | |
|---|---|---|
| 9,131,859 B2 | 9/2015 | Sawanoi et al. |
| 11,576,584 B2 * | 2/2023 | Jang ..................... A61B 5/7203 |
| 2009/0326393 A1 * | 12/2009 | Sethi ..................... A61B 5/021 |
| | | 600/494 |
| 2011/0245628 A1 * | 10/2011 | Baker, Jr. ............. A61B 5/0205 |
| | | 600/300 |
| 2013/0324859 A1 | 12/2013 | Park et al. |
| 2014/0073865 A1 | 3/2014 | Rodriguez-Llorente et al. |
| 2018/0110473 A1 | 4/2018 | Kim |

FOREIGN PATENT DOCUMENTS

| | | |
|---|---|---|
| KR | 10-2007-0075515 A | 7/2007 |
| KR | 10-2011-0032107 A | 3/2011 |
| KR | 10-2012-0058243 A | 6/2012 |
| KR | 10-1656740 B1 | 9/2016 |
| KR | 10-2016-0126232 A | 11/2016 |

OTHER PUBLICATIONS

Elgendi, "On the Analysis of Fingertip Photoplethysmogram Signals", 2012, Current Cardiology Reviews, vol. 8, No. 1, 12 pages total.

Huang, et al., "Decomposition Analysis of Digital vol. Pulse Signal Using Multi-Model Fitting", 2014, XIII Mediterranean Conference on Medical and Biological Engineering and Computing 2013, IFMBE Proceedings 41, 2 pages total.

Jang et al., "Framework for Automatic Delineation of Second Derivative of Photoplethysmogram: A Knowledge-based Approach", 2014, Journal of Medical and Biological Engineering, vol. 34, No. 6, 7 pages total.

Communication dated Jan. 2, 2019, issued by the European Patent Office in counterpart European Application No. 18185204.7.

Ming Hong, "A Real-time Pulse Wave Detection Device Basing on Signal Envelope", 5th International Conference on BioMedical Engineering and Informatics (BMEI), IEEE, XP032395600, Oct. 16, 2012, pp. 812-816.

Melpo Pittara et al., "Estimation of Pulse Rate from Ambulatory PPG using Ensemble Empirical Mode Decomposition and Adaptive Thresholding", 39th Annual International Conference of the IEEE Engineering in Medicine and Biology Society (EMBC), IEEE, XP033152661, Jul. 11, 2017, pp. 2916-2919.

Matti Huotari et al., "Infrared and red PPG signals analysis of the healthy subjects and clinical patients", 15th Biennial Baltic Electronics Conference (BEC), IEEE, XP033005342, Tallinn, Estonia, Oct. 3, 2016, pp. 111-114.

* cited by examiner

APPARATUS AND METHOD FOR DETECTING BIO-SIGNAL FEATURE

CROSS-REFERENCE TO RELATED APPLICATION(S)

This application is a divisional application of U.S. application Ser. No. 16/044,020, filed Jul. 24, 2018, which claims priority from Korean Patent Application No. 10-2017-0094310, filed on Jul. 25, 2017 in the Korean Intellectual Property Office, the disclosure of which is incorporated herein by reference in its entirety.

BACKGROUND

1. Field

Apparatuses and methods consistent with exemplary relate to detecting a bio-signal feature.

2. Description of Related Art

Healthcare technology has attracted much attention due to the rapid entry into an aging society and relevant social problems such as increase in medical expenses. Accordingly, medical devices that can be utilized by hospitals and inspection agencies as well as small-sized medical devices that can be carried by individuals such as wearable devices are being developed. In addition, such a small-sized medical device is worn by a user in the form of a wearable device capable of directly measuring cardiovascular health status such as blood pressure or the like, so that the user can directly measure and manage cardiovascular health status.

Therefore, recently, studies on a method of estimating a blood pressure by analyzing a bio-signal for minimization of a device, particularly, a method of stably detecting features of a bio-signal, which are used in estimating the blood pressure, with a small amount of computation, have been conducted.

SUMMARY

One or more exemplary embodiments provide a bio-signal feature detection apparatus and method capable of detecting a bio-signal feature based on the bio-signal and an envelope signal.

According to an aspect of an exemplary embodiment, there is provided an apparatus for detecting a bio-signal feature, the apparatus including: a bio-signal acquirer configured to acquire a bio-signal; and a processor configured to generate an envelope signal of the bio-signal, and detect at least one feature of the bio-signal based on a difference between the envelope signal and the bio-signal.

The bio-signal may be a pulse wave signal, a first-order differential signal of the pulse wave signal, or a second-order differential signal of the pulse wave signal.

The bio-signal acquirer may include at least one of a photoplethysmogram (PPG) sensor that detects a PPG signal or a pressure pulse wave signal that corresponds to the bio-signal, and a communication interface configured to receive the bio-signal from an external device.

The candidate features may include a reflection wave component constituting the bio-signal.

The processor may detect at least one peak point or at least one valley point in one period of the bio-signal, and may generate the envelope signal by linearly connecting a start point, the at least one peak point or valley point, and an end point of the bio-signal in the period.

The processor may determine an effective range of the bio-signal by setting a minimum point in the period of the bio-signal as the start point and setting a last zero crossing point or a last valley point in the period of the bio-signal as the end point.

The processor may calculate a plurality of separate areas between a first graph representing the envelope signal and a second graph representing the bio-signal, and may detect, as the at least one feature, a peak point or a valley point from a largest area of the plurality of separate areas between the first graph and the second graph.

The processor may divide an effective range of the bio-signal into a plurality of sections based on a peak point or a valley point within the effective range, and may calculate the plurality of separate areas by summing differences between the envelope signal and the bio-signal in each of the plurality of sections.

The processor may correct the calculated plurality of separate areas using a scaling function.

The scaling function may be generated based on probability that a feature exists in the bio-signal.

The processor may perform signal smoothing on the bio-signal.

The processor may divide an effective range of the bio-signal into a plurality of sections, may calculate an area of each of the plurality of sections by summing absolute values of differences between the envelope signal and the bio-signal in each of the plurality of sections, may detect at least one of peak points and valley points of largest N sections as candidate features, among the plurality of sections, and may detect the at least one feature from the candidate features, based on priori information, wherein N is a natural number.

The priori information may include information about a position at which the at least one feature is detected.

The processor may detect one of the candidate features that is closest to the priori information as the at least one feature.

The processor may update the priori information based on the detected at least one feature.

According to an aspect of another exemplary embodiment, there is provided a method of detecting a bio-signal feature, including: acquiring a bio-signal; generating an envelope signal of the bio-signal; and detecting at least one feature of the bio-signal based a difference between the envelope signal and the bio-signal.

The bio-signal may be a pulse wave signal, a first-order differential signal of the pulse wave signal, or a second-order differential signal of the pulse wave signal.

The pulse wave signal may include a photoplethysmogram (PPG) signal and a pressure pulse wave signal.

The at least one feature may represent a reflection wave component constituting the bio-signal.

The generating the envelope signal may include: detecting at least one peak point or at least one valley point in one period of the bio-signal; and generating the envelope signal by linearly connecting a start point, the at least one peak point or valley point, and an end point of the bio-signal in the period.

The generating the envelope signal may further include determining an effective range of the bio-signal by setting a minimum point in the period of the bio-signal as the start point and setting a last zero crossing point or a last valley point in the period of the bio-signal as the end point.

The detecting the at least one feature may include: calculating a plurality of separate areas between a first graph representing the envelop signal and a second graph representing the bio-signal; and detecting, as the at least one feature, a peak point or a valley point from a largest area of the plurality of separate areas between the first graph and the second graph.

The detecting the at least one feature may further include: dividing an effective range of the bio-signal into a plurality of sections based on a peak point or a valley point within the effective range.

The calculating the plurality of separate areas may include correcting the calculated plurality of separate areas using a scaling function.

The scaling function is generated based on probability that a feature exists in the bio-signal.

The method may further include performing signal smoothing on the bio-signal, so that the envelope signal is generated based on the bio-signal, on which the signal smoothing is performed.

The detecting the at least one feature may include: dividing an effective range of the bio-signal into a plurality of sections; calculating an area of each of the plurality of sections by summing absolute values of differences between the envelope signal and the bio-signal in each of the plurality of sections; detecting at least one of peak points and valley points of largest N sections, among the plurality of sections, as the candidate features; and detecting the at least one feature from the candidate features based on priori information, wherein N is a natural number.

The priori information may include information about a position at which the at least one feature is detected.

The detecting the at least one critical feature may include detecting one of the candidate features that is closest to the priori information as the at least one feature.

The method may further include updating the priori information based on the detected at least one feature.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
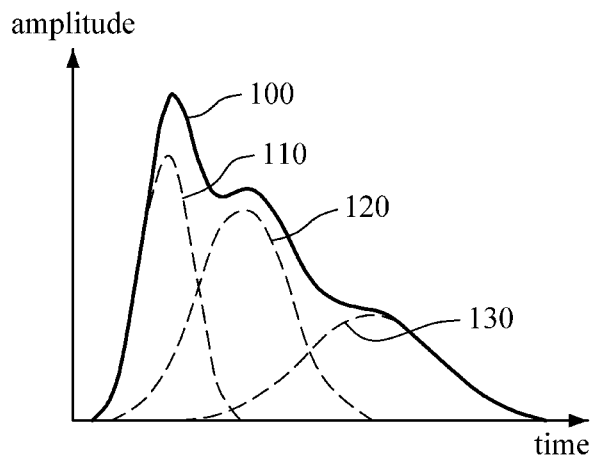
FIG. 1 is a diagram illustrating a bio-signal according to one exemplary embodiment.

Exemplary embodiments are described in greater detail below with reference to the accompanying drawings.

Throughout the drawings and the detailed description, unless otherwise described, the same drawing reference numerals will be understood to refer to the same elements, features, and structures. The relative size and depiction of these elements may be exaggerated for clarity, illustration, and convenience. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described in below are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

Meanwhile, an apparatus for detecting a bio-signal feature described herein may be implemented as a software module or in the form of a hardware chip and be mounted in an electronic device. In this case, the electronic device may include a mobile phone, a smart phone, a notebook computer, a personal digital assistant (PDA), a portable multimedia player (PMP), a navigation system, an MP3 player, a digital camera, a wearable device, etc., and the wearable device may include various types of wearable devices, such as a wristwatch type, a wristband type, a ring type, a belt-type, a necklace type, an ankle band type, a thigh band type, a forearm band type, and the like. However, the electronic device is not limited to the above mentioned examples, and the wearable device is also not limited to the above-described examples.

FIG. 1 is a diagram illustrating a bio-signal according to one exemplary embodiment. Specifically, FIG. 1 illustrates one embodiment of a photoplethysmogram (PPG) signal.

Referring to FIG. 1, a waveform of a PPG signal 100 may be a summation of a propagation wave 110 propagating from the heart to peripheral parts of a body and reflection waves 120 and 130 returning from the peripheral parts of the body. In the illustrated example, the PPG signal 100 is a summation of the propagation wave 110 and the reflection waves 120 and 130.

Figure 2:
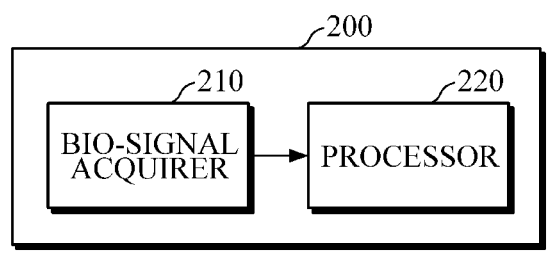
FIG. 2 is a block diagram illustrating an apparatus for detecting a bio-signal feature according to one exemplary embodiment.

FIG. 2 is a block diagram illustrating an apparatus for detecting a bio-signal feature according to one exemplary embodiment.

Referring to FIG. 2, the apparatus 200 for detecting a feature of a bio-signal includes a bio-signal acquirer 210 and a processor 220.

The bio-signal acquirer 210 may acquire a bio-signal of one period. In this case, the bio-signal may be a pulse wave signal (e.g., a PPG signal or a pressure pulse wave signal), a first-order differential signal of a pulse wave signal, or a second-order differential signal of a pulse wave signal.

According to one exemplary embodiment, the bio-signal acquirer 210 may acquire a bio-signal from an external device which senses and/or stores the bio-signal. In this case, the bio-signal acquirer 210 may correspond to a communication interface which uses various communication technologies, such as Bluetooth, Bluetooth low energy (BLE), near field communication (NFC), wireless local area network (WLAN), ZigBee, infrared data association (IrDA), Wi-Fi direct, ultra-wideband, Ant+, Wi-Fi, radio frequency identification (RFID), 3G communication, 4G communication, and 5G communication.

According to another exemplary embodiment, the bio-signal acquirer 210 may include various sensors, such as an electrocardiography (ECG) sensor that measures an electrical activity of the heart by using electrodes placed on the skin of a subject, or a PPG sensor that optically senses the rate of blood flow as controlled by the heart's pumping action, to acquire a bio-signal.

The processor 220 may generate an envelope signal from the acquired bio-signal and detect a feature of the bio-signal using difference between the generated envelope signal and the bio-signal. In this case, the envelope signal may be divided into an upper envelope signal generated based on a peak point of the bio-signal and a lower envelope signal generated based on a valley point of the bio-signal.

Meanwhile, the feature may be defined as a point that represents a reflection wave component (e.g., the reflection wave components 120 and 130 of FIG. 1) constituting the bio-signal.

Hereinafter, an exemplary embodiment using the upper envelope signal, an exemplary embodiment using the lower envelope signal, and an exemplary embodiment using both the upper and lower envelope signals will be separately described.

<Exemplary Embodiment Using an Upper Envelope Signal>

The processor 220 may determine an effective range of the bio-signal. In this case, the effective range has a minimum point of the bio-signal as a start point and the last zero crossing point or the last valley point of the bio-signal as an end point. That is, the processor 220 may detect the minimum point and the last zero crossing point or the last valley point of the bio-signal, and determine that a range from the minimum point to the last zero crossing point or the last valley point as the effective range for detecting a feature.

The processor 220 may detect at least one peak point from the effective range of the bio-signal and generate the upper envelope signal by linearly connecting the start point of the effective range, the detected at least one peak point and the end point of the effective range.

The processor 220 may calculate a difference between the upper envelope signal and the bio-signal. For example, the processor 220 may calculate the difference between the upper envelope signal and the bio-signal by subtracting the bio-signal from the upper envelope signal. In this case, the processor 220 may correct the difference between the upper envelope signal and the bio-signal using a scaling function. The scaling function may be generated based on probability information on which a feature may appear, and then be stored in an internal/external memory of the apparatus 200 for detecting a feature of a bio-signal.

The processor 220 may divide the effective range of the bio-signal into a plurality of sections based on the peak points within the effective range, and calculate an area of each of the sections by summing absolute values of the differences between the upper envelope signal and the bio-signal in each section. For example, when two peak points, a first peak point and a second peak point, are present within the effective range, the processor 220 may divide the effective range into three sections, a first section starting from the start point of the effective range to the first peak point, a second section from the first peak point to the second peak point, and a third section from the second peak point to the end point of the effective range, and calculate the area of each of the sections by summing absolute values of the differences between the envelope signal and the bio-signal in each section.

The processor 220 may extract a section (hereinafter referred to as a "maximum area section") having the largest area from the plurality of segmented sections based on the calculated area of each of the sections and detect a start point (peak point) and/or a valley point of the extracted maximum area section as a feature of the bio-signal.

<Exemplary Embodiment Using a Lower Envelope Signal>

The processor 220 may determine an effective range of the bio-signal. In this case, the effective range may have a minimum point of the bio-signal as a start point and the last zero crossing point or the last valley point of the bio-signal as an end point. That is, the processor 220 may detect a minimum point and the last zero-crossing point or the last valley point of the bio-signal, and determine a range from the minimum point to the last zero crossing point or the last valley point as the effective range for detecting a feature of the bio-signal.

The processor 220 may detect at least one valley point within the effective range of the bio-signal and generate a lower envelop signal by linearly connecting the start point of the effective range, the detected at least one valley point, and the end point of the effective range.

The processor 220 may calculate a difference between the bio-signal and the lower envelope signal. For example, the processor 220 may calculate the difference between the bio-signal and the lower envelope signal by subtracting the lower envelope signal from the bio-signal. In this case, the processor 220 may correct the difference between the bio-signal and the lower envelope signal using a scaling function.

The processor may divide the effective range into a plurality of sections based on the valley points within the effective range, and calculate the area of each of the sections by summing absolute values of the differences between the envelope signal and the bio-signal in each section. For example, when there are two valley points, a first valley point and a second valley point, in the effective range, the processor 220 may divide the effective range into three sections, a first section from the start point of the effective range to the first valley point, a second section from the first valley point to the second valley point, and a third section from the second valley point to the end point of the effective range, and calculate the area of each of the sections by summing absolute values of the differences between the envelope signal and the bio-signal in each section.

The processor 220 may extract a maximum area section from among the plurality of sections based on the calculated area of each of the sections, and detect a peak point and/or an end point (valley point) of the extracted maximum area as a feature of the bio-signal.

<Exemplary Embodiment Using an Upper Envelope Signal and a Lower Envelope Signal>

The processor 220 may determine an effective range of a bio-signal. In this case, the effective range may have a minimum point of the bio-signal as a start point and the last zero crossing point or the last valley point of the bio-signal as an end point. That is, the processor 220 may detect the minimum point and the last zero-crossing point or the last valley point of the bio-signal, and determine a range from the minimum point to the last zero crossing point or the last valley point as the effective range for detecting a feature of the bio-signal.

The processor 220 may detect at least one peak point from the effective range of the bio-signal, and generate an upper envelope signal by linearly connecting the start point of the effective range to the detected at least one peak point, and then to the end point of the effective range. The processor 220 may generate a lower envelope signal by linearly connecting the start point of the effective range to the detected at least one peak point, and then to the end point of the effective range.

The processor 220 may calculate a difference between the upper envelope signal and the bio-signal and a difference between the bio-signal and the lower envelope signal. For example, the processor 220 may calculate the difference between the upper envelope signal and the bio-signal by subtracting the bio-signal from the upper envelope signal and calculate the difference between the bio-signal and the lower envelope signal by subtracting the lower envelope signal from the bio-signal. In this case, the processor 220 may correct the difference between the upper envelope signal and the bio-signal and the difference between the lower envelope signal and the bio-signal using a scaling function.

The processor 220 may divide the effective range of the bio-signal into a plurality of sections (hereinafter referred to as "peak-based sections") based on the peak points within the effective range, and calculate an area of each of the sections (hereinafter referred to as "an area of each peak-based section") by summing absolute values of the differences between the upper envelope signal and the bio-signal in each section. In addition, the processor 220 may divide the effective range of the bio-signal into a plurality of sections (hereinafter referred to as "valley-based sections") based on the valley points within the effective range and calculate an area of each of the sections (hereinafter referred to as "an area of each valley-based section") by summing absolute values of the differences between the lower envelope signal and the bio-signal in each section.

The processor 220 may calculate an area of each integrated section by integrating the area of each peak-based section and the area of each valley-based section.

According to one exemplary embodiment, the processor 220 may calculate an area of each integrated section by applying a first weight (e.g., 0.6) to the area of each peak-based section, applying a second weight (e.g., 0.4) to the area of each valley-based section, and summing the areas of the mutually corresponding sections. In this case, the first weight and the second weight may be experimentally determined and the $(n+1)^{th}$ peak-based section and the $n^{th}$ valley-based section may mutually correspond to each other. For example, it is assumed that, in a case in which three peak-based sections (e.g., a first peak-based section to a third peak-based section) and two valley-based sections (e.g., a first valley-based section and a second valley-based section) are present, an area of the first peak-based section is 10, an area of the second peak-based section is 520, an area of the third peak-based section is 100, an area of the first valley-based section is 300, an area of the second valley-based section is 200, the first weight is 0.6, and the second weight is 0.4. In this case, the processor 220 may apply the first weight of 0.6 to the area of 10 of the first peak-based section and add 0 to the resulting value, given that there is no valley-based section corresponding to the first peak-based section, to calculate an integrated area of the first peak-based section, which has a result value of 6 as follows:

$$10 \times 0.6 + 0 = 6.$$

In addition, the processor 220 may apply the first weight of 0.6 to the area of 520 of the second peak-based section, apply the second weight of 0.4 to the area of 300 of the first valley-based section, and sum the weighted areas to calculate an integrated area of the second peak-based section (or the first valley-based section), which has a result value of 432 as follows:

$$(520 \times 0.6) + (300 \times 0.4) = 432$$

Also, the processor 220 may apply the first weight of 0.6 to the area of 100 of the third peak-based section, apply the second weight of 0.4 to the area of 200 of the second valley-based section and sum the weighted areas to calculate an integrated area of the third peak-based section (or the second valley-based section), which has a result value of 140 as follows:

$$(100 \times 0.6) + (200 \times 0.4) = 140$$

The processor 220 may extract a section having the largest integrated area (hereinafter referred to as a "maximum integrated area section") from among the plurality of sections, and detect a peak point and/or a valley point of the extracted maximum integrated area section as a feature of the bio-signal. For example, in the above example, the processor 220 may extract the second peak-based section (or the first valley-based section) whose integrated area is the largest and detect a start point (peak point) and/or a valley point of the second peak-based section (or a peak point and/or a valley point of the first valley-based section) as the feature of the bio-signal.

Meanwhile, the detected features may be used to estimate a blood pressure of the subject from which the bio-signal is measured. For example, various characteristic values (e.g., time, amplitude, etc.) of the bio-signal may be calculated using the features detected by the apparatus 200 for detecting a bio-signal feature and it is possible to estimate the blood pressure of the subject using the various calculated characteristic values and a pre-stored blood pressure estimation equation.

Figure 3:
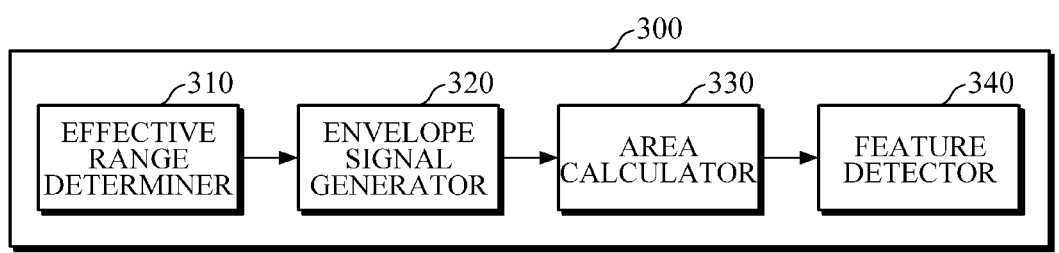
FIG. 3 is a block diagram illustrating a processor according to one exemplary embodiment.

FIG. 3 is a block diagram illustrating a processor according to one exemplary embodiment. A processor 300 of FIG. 3 may be one exemplary embodiment of the processor 220 of FIG. 2.

Referring to FIG. 3, the processor 300 includes an effective range determiner 310, an envelope signal generator 320, an area calculator 330, and a feature detector 340.

The effective range determiner 310 may determine an effective range of a bio-signal. For example, the effective range has a minimum point of the bio-signal as a start point and the last zero crossing point or the last valley point of the bio-signal as an end point. The effective range determiner 310 may detect the minimum point and the last zero crossing point or the last valley point of the bio-signal, and determine that a range from the minimum point to the last zero crossing point or the last valley point as the effective range for detecting a feature.

The envelope signal generator 320 may generate an envelope signal of the bio-signal.

For example, the envelope signal generator 320 may detect at least one peak point from the effective range of the bio-signal and generate an upper envelope signal by linearly connecting the start point of the effective range to the detected at least one peak point, and then to the end point of the effective range. The envelope signal generator 320 may generate a lower envelope signal by connecting the start point of the effective range to the detected at least one valley point, and then to the end point of the effective range.

The area calculator 330 may calculate a difference between the bio-signal and at least one of the upper envelope signal and the lower envelope signal.

According to one exemplary embodiment, in the case in which the envelope signal generator 320 generates the upper envelope signal, the area calculator 330 may calculate a difference between the upper envelope signal and the bio-signal by subtracting the bio-signal from the upper envelope signal.

According to another exemplary embodiment, in a case in which the envelope signal generator 320 generates the lower envelope signal, the area calculator 330 may calculate a difference between the lower envelope signal and the bio-signal by subtracting the lower envelope signal from the bio-signal.

Meanwhile, the area calculator 330 may correct the difference between the upper envelope signal and the bio-signal and the difference between the bio-signal and the lower envelope signal using a scaling function.

The area calculator 330 may divide the effective range based on the peak points or the valley point within the effective range and calculate an area of each section by summing absolute values of the differences between the envelope signal and the bio-signal in each section.

According to one exemplary embodiment, in a case in which the envelope signal generator 320 generates the upper envelope signal, the area calculator 330 may divide the effective range of the bio-signal into a plurality of sections based on the peak points within the effective range, and calculate an area of each of the sections by summing absolute values of the differences between the upper envelope signal and the bio-signal in each section.

According to another exemplary embodiment, in a case in which the envelope signal generator 320 generates the lower envelope signal, the area calculator 330 may divide the effective range into a plurality of sections on the valley point within the effective range, and calculate the area of each of the sections by summing the differences between the envelope signal and the bio-signal in each section.

According to still another exemplary embodiment, in a case in which the envelope signal generator 320 generates both the upper envelope signal and the lower envelope signal, the area calculator 330 may divide the effective range into a plurality of peak-based sections and into a plurality of valley-based sections, respectively, calculate an area of each peak-based section by summing differences between the upper envelope signal and the bio-signal in each peak-based section, and calculate an area of each valley-based section by summing differences between the bio-signal and the lower envelope signal in each valley-based section. In addition, the area calculator 330 may calculate an area of each integrated section by applying a first weight to the area of each peak-based section, applying a second weight to the area of each valley-based section, and thereafter, summing areas of the mutually corresponding sections.

The feature detector 340 may select a maximum area section based on the calculated areas for each section and detect a peak point and/or a valley point of the selected maximum area section as a feature of the bio-signal.

According to one exemplary embodiment, the feature detector 340 may select a maximum area section from the plurality of peak-based sections and detect a start point (peak point) of the selected maximum area section and/or a valley point thereof as a feature of the bio-signal.

According to another exemplary embodiment, the feature detector 340 may select a maximum area section from the plurality of valley-based sections and detect a peak point of the selected maximum area section and/or an end point (valley point) thereof as a feature of the bio-signal.

According to still another exemplary embodiment, the feature detector 340 may extract a maximum integrated area section from the plurality of sections (the plurality of peak-based sections and the valley-based sections) and detect a peak point of the extracted maximum integrated area section and/or a valley point thereof as a feature of the bio-signal.

Figure 4:
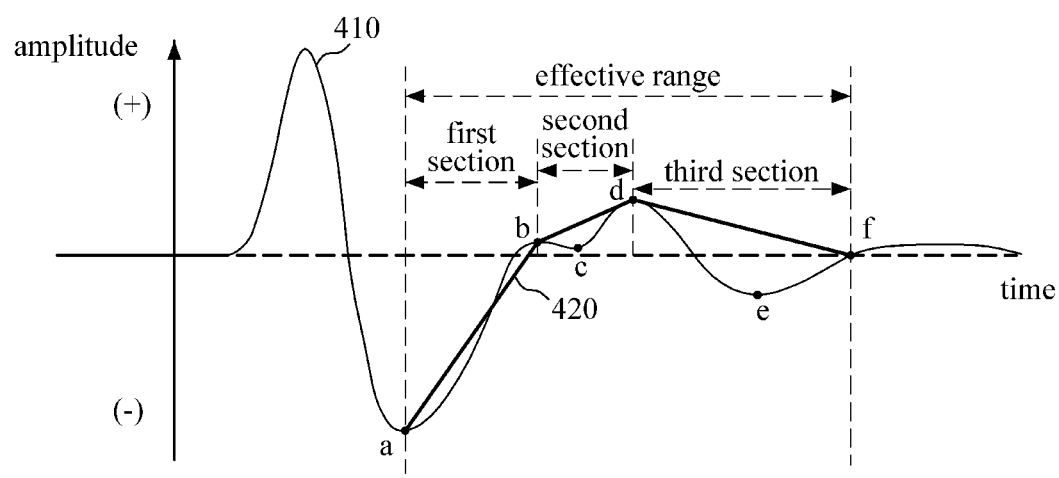
FIG. 4 is a diagram for describing an example of detecting a feature using an upper envelope signal.

FIG. 4 is a diagram for describing an example of detecting a feature using an upper envelope signal. In FIG. 4, a bio-signal 410 represents a second-order differential signal of a pulse wave signal.

Referring to FIGS. 3 and 4, the effective range determiner 310 detects a minimum point a and the last zero crossing point f from the bio-signal 410 and determines a range from the minimum point a to the last zero crossing point f as an effective range.

The envelope signal generator 320 detects peak points b and d in the effective range and generate an upper envelope signal 420 by connecting the start point a of the effective range, the peak points b and d, and the end point f of the effective range.

The area calculator 330 calculates a difference between the upper envelope signal 420 and the bio-signal 410 by subtracting the bio-signal 410 from the upper envelope signal 420. In this case, the area calculator 330 may correct the difference between the upper envelope signal 420 and the bio-signal 410 using a scaling function.

The area calculator 330 divides the effective range into three sections (a first section, a second section, and a third section) based on the peak points b and d in the effective range and calculates an area of each section by summing absolute values of the differences between the upper envelope signal 420 and the bio-signal 410 in each section.

The feature detector 340 selects a third section that is a maximum area section from among the three sections (i.e., the first section to the third section) based on the calculated areas for each section, and detects a start point d of the third section and/or a valley point e as a feature of the bio-signal 410.

Figure 5:
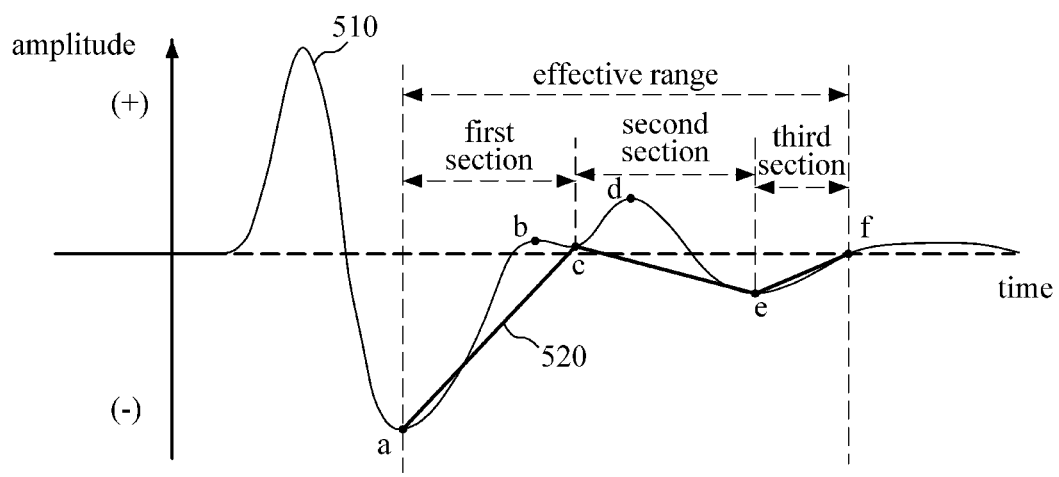
FIG. 5 is a diagram for describing an example of detecting a feature using a lower envelope signal.

FIG. 5 is a diagram for describing an example of detecting a feature using a lower envelope signal. In FIG. 5, a bio-signal 510 represents a second-order differential signal of a pulse wave signal.

Referring to FIGS. 3 and 5, the effective range determiner 310 detects a minimum point a and the last zero crossing point f from the bio-signal 510 and determine a range from the minimum point a to the last zero crossing point f as an effective range.

The envelope signal generator 320 detects valley points c and e in the effective range and generates a lower envelope signal 520 by connecting the start point a of the effective range, the valley points c and e in the effective range, and the end point f of the effective range.

The area calculator 330 calculates a difference between the bio-signal 510 and the lower envelope signal 520 by subtracting the lower envelope signal 520 from the bio-signal 510. In this case, the area calculator 330 may correct the difference between the bio-signal 510 and the lower envelope signal 520 using a scaling function.

The area calculator 330 divides the effective range into three sections (a first section, a second section, and a third section) based on the valley points c and e in the effective range and calculates an area of each section by summing absolute values of the differences between the bio-signal 510 and the lower envelope signal 520 in each section.

The feature detector 340 selects the second section that is a maximum area section from among the three sections (i.e., the first section to the third section) based on the calculated areas for each section, and detects a peak point d of the second section and/or an end point e thereof as a feature of the bio-signal 510.

Figure 6A:
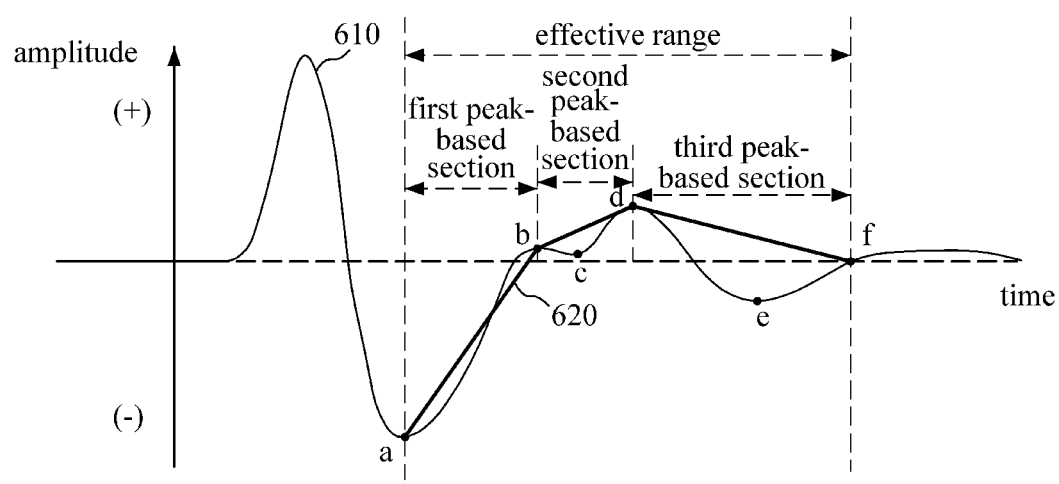
FIGS. 6A and 6B are diagrams for describing an example of detecting a feature using both an upper envelope signal and a lower envelope signal.
Figure 6B:
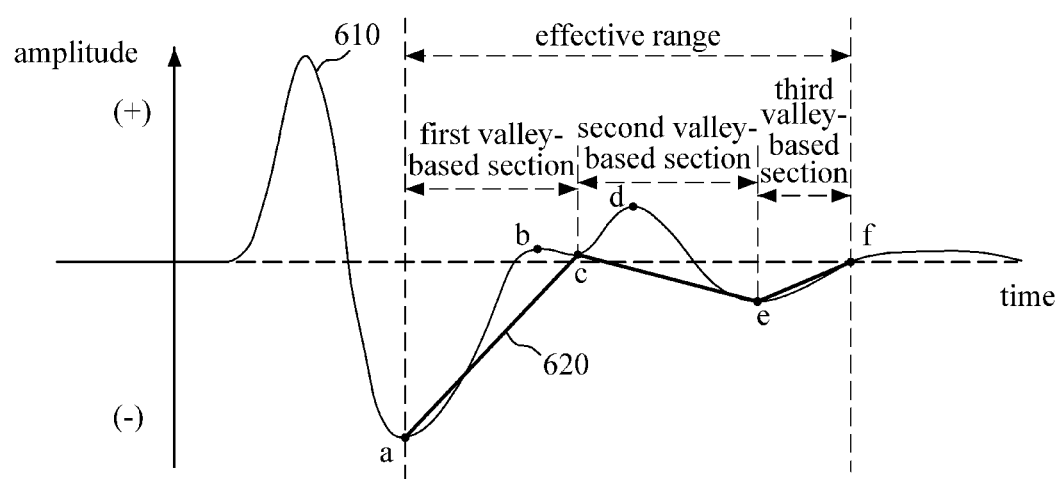

FIGS. 6A and 6B are diagrams for describing an example of detecting a feature using both an upper envelope signal and a lower envelope signal. In FIGS. 6A and 6B, a bio-signal 610 represents a second-order differential signal of a pulse wave signal.

Referring to FIGS. 3, 6A and 6B, the effective range determiner 310 detects a minimum point a and the last zero crossing point f of the bio-signal 610 and determines a range from the minimum point a to the last zero crossing point f as an effective range.

The envelope signal generator 320 detects peak points b and d in the effective range, and generates an upper envelope signal 620 by connecting the start point a of the effective range, the peak points b and d, and the end point f of the effective range, with reference to FIG. 6A. The envelope signal generator 320 detects valley points c and e in the effective range, and generates a lower envelope signal 520 by connecting the start point a of the effective range, the valley points c and e in the effective range, and an end point f of the effective range, with reference to FIG. 6B.

The area calculator 330 calculates a difference between the upper envelope signal 620 and the bio-signal 610 by subtracting the bio-signal 610 from the upper envelope signal 620, with reference to FIG. 6A. In addition, the area calculator 330 calculates a difference between the bio-signal 610 and the lower envelope signal 630 by subtracting the lower envelope signal 630 from the bio-signal 610, with reference to FIG. 6B. The area calculator 330 may correct the difference between the upper envelope signal 620 and the bio-signal 610 and the difference between the bio-signal 610 and the lower envelope signal 630 using a scaling function.

The area calculator 330 divides the effective range into three sections (e.g., a first peak-based section, a second peak-based section, and a third peak-based section) based on the peak points b and d in the effective range and calculates an area of each section by summing absolute values of the differences between the upper envelope signal 620 and the bio-signal 610 in each peak-based section, with reference to FIG. 6A). In addition, the area calculator 330 divides the effective range into three sections (e.g., a first valley-based section, a second valley-based section, and a third valley-based section) based on the valley points c and e in the effective range and calculates an area of each section by summing the differences between the bio-signal 610 and the lower envelope signal 630 in each valley-based section, with reference to FIG. 6B.

The area calculator 330 calculates an area of each integrated section by applying a first weight to the area of each peak-based section, applying a second weight to the area of each valley-based section, and thereafter, summing areas of the mutually corresponding sections. In this case, the second peak-based section corresponds to the first valley-based section, and the third peak-based section corresponds to the second valley-based section. On the other hand, there is no valley-based section that corresponds to the first peak-based section and there is no peak-based section that corresponds to the third valley-based section.

The feature detector 340 selects the third peak-based section that is a maximum integrated area section from among the three peak-based sections (i.e., the first peak-based section, the second peak-based section, and the third peak-based section) based on the calculated areas of each of integrated sections, and detects a start point d of the third peak-based section and/or a valley point e thereof as a feature of the bio-signal 610. Alternatively, or in addition to the third peak-based section, the feature detector 340 may select the second valley-based section that is a maximum integrated area section from among the three valley-based sections (i.e., the first valley-based section, the second valley-based section, and the third valley-based section) based on the calculated areas of each of integrated sections, and detect a peak point d of the second valley-based section and/or an end point e thereof as a feature of the bio-signal 610.

Figure 7:
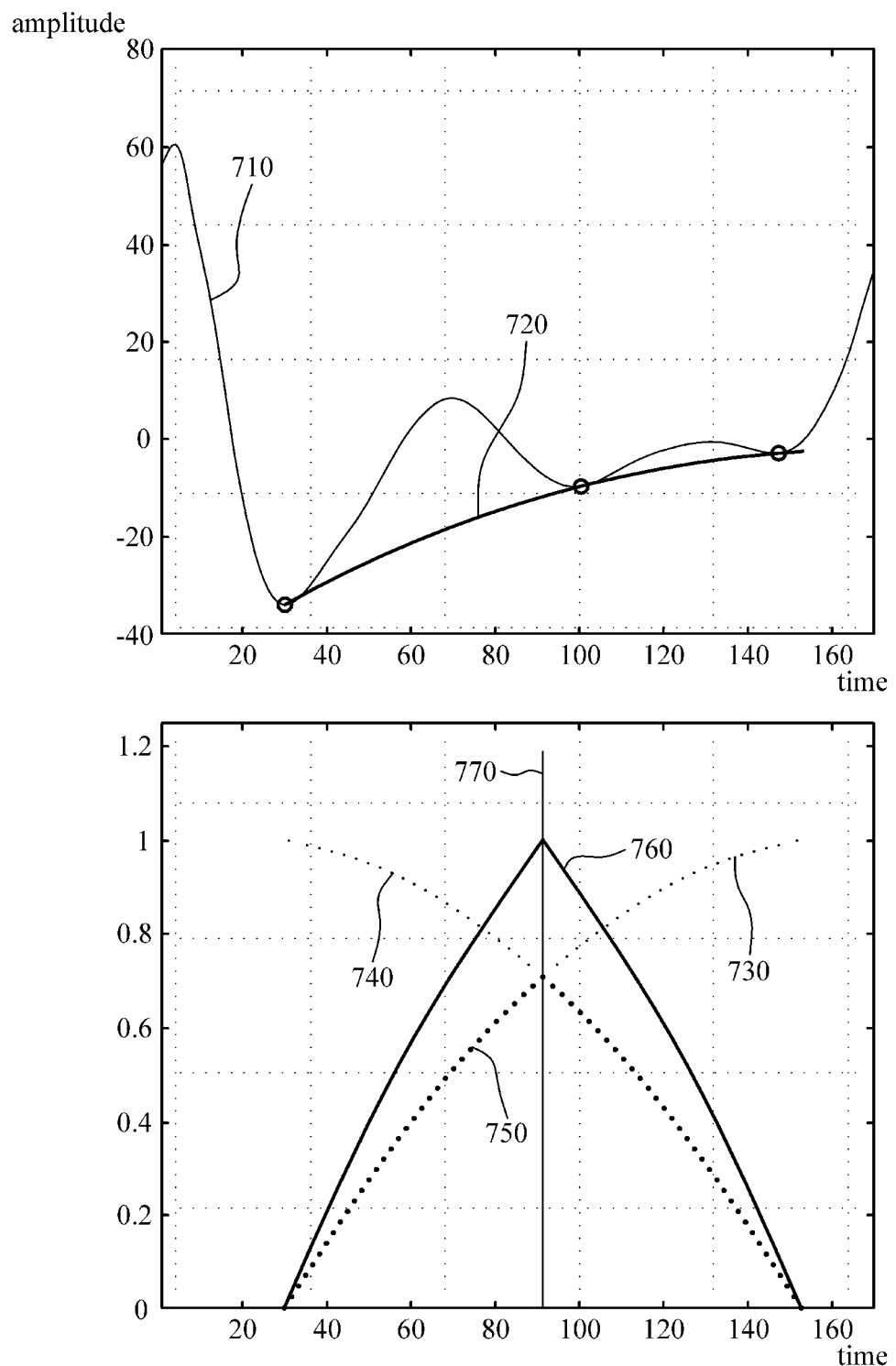
FIG. 7 is a diagram for describing a method of generating a scaling function.

FIG. 7 is a diagram for describing a method of generating a scaling function.

A feature according to one exemplary embodiment may mostly appear near an inflection point of a lower envelope signal. Therefore, a scaling function may be generated based on such a characteristic.

With reference to FIG. 2, the processor 220 or an external device that communicates with the processor may generate a scaling function. Hereinafter, it is assumed that the processor 220 generates the scaling function and a bio-signal 710 is a second-order differential signal of a pulse wave signal.

Referring to FIG. 7, the processor 220 may form a best-fit line that passes through a start point and two valley points of the bio-signal to generate a lower envelope signal 720 in a curved-shape. The processor 220 may generate a scaled lower envelope signal 730 by scaling the lower envelope signal 720 to have a range of 0 to 1.

The processor 220 may generate a signal 740 that is horizontally symmetric to the lower envelope signal 730 scaled based on a time central axis 770.

The processor 220 may generate a signal based on the scaled lower envelope signal 730 and the horizontally symmetric signal 740 and generate a scaling function 760 by scaling the generated signal 750 to have a range of 0 to 1.

Figure 8:
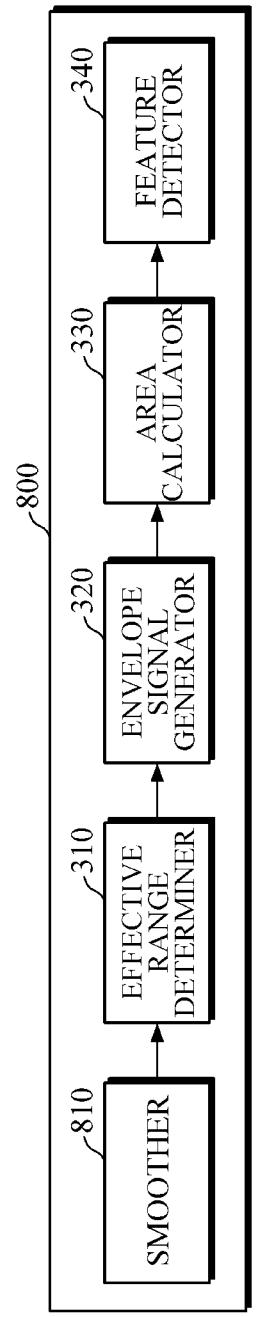
FIG. 8 is a block diagram illustrating a processor according to another exemplary embodiment.

FIG. 8 is a block diagram illustrating a processor according to another exemplary embodiment. A processor 800 of FIG. 8 may be one exemplary embodiment of the processor 220 of FIG. 2.

Referring to FIG. 8, the processor 800 includes an effective range determiner 310, an envelope signal generator 320, an area calculator 330, a feature detector 340, and a smoother 810. Here, the effective range determiner 310, the envelope signal generator 320, the area calculator 330, and the feature detector 340 have been described with reference to FIG. 3, and hence detailed descriptions thereof will be omitted.

The smoother 810 may smooth a bio-signal. For example, the smoother 810 may perform single smoothing by removing noise from the bio-signal using a low-pass filter (e.g., a moving average filter).

Figure 9:
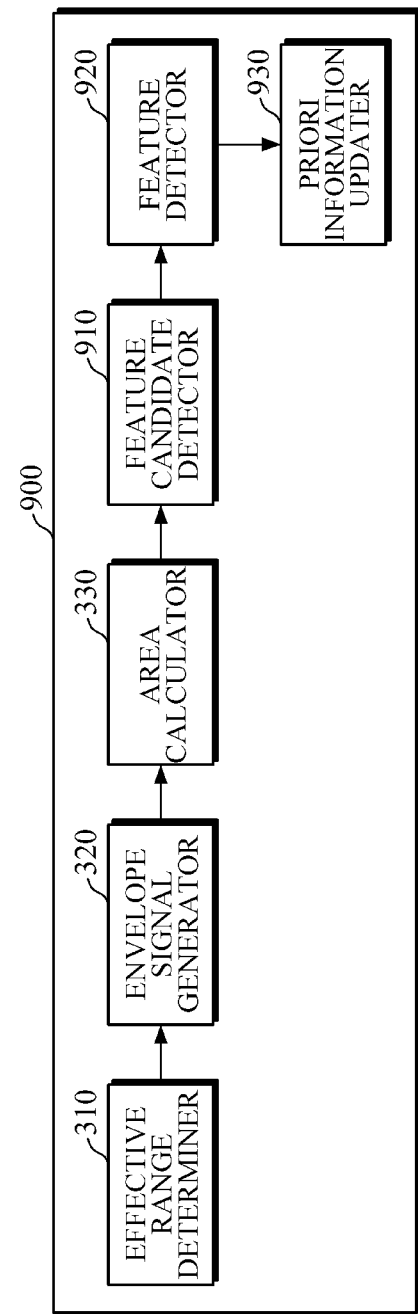
FIG. 9 is a block diagram illustrating a processor according to still another exemplary embodiment.

FIG. 9 is a block diagram illustrating a processor according to still another exemplary embodiment. A processor 900 of FIG. 9 may be one exemplary embodiment of the processor 220 of FIG. 2.

Referring to FIG. 9, the processor 900 includes an effective range determiner 310, an envelope signal generator 320, an area calculator 330, a feature candidate detector 910, a feature detector 920, and a priori information updater 930. Here, the effective range determiner 310, the envelope signal generator 320, and the area calculator 330 have been described with reference to FIG. 3, and hence detailed descriptions thereof will be omitted.

The feature candidate detector 910 may select top N sections (N is an arbitrary natural number) having large areas based on areas of each section calculated by the area calculator 330, and detect peak points and/or valley points in the selected N sections as feature candidates. For example, an effective range may be divided into five sections (e.g., a first section to a fifth section), and relative sizes of areas of each of the sections are expressed as follows: the third section>the fourth section>the second section>the first section>the fifth section, wherein N is 2. In this case, the feature candidate detector 910 may detect a peak point and/or a valley point of the third section and a peak point and/or a valley point of the fourth section as feature candidates.

The feature detector 920 may detect one of the feature candidates as a feature based on pre-stored priori information. In this case, the priori information may be information about a position from which the feature is detected. The priori information may be derived by learning feature detection results. According to one exemplary embodiment, the feature detector 920 may calculate distances between the priori information and each of the feature candidates, and detect the feature candidate that is closest to the priori information as a feature of the bio-signal.

The priori information updater 930 may update the pre-stored priori information based on position information of the detected feature.

Figure 10:
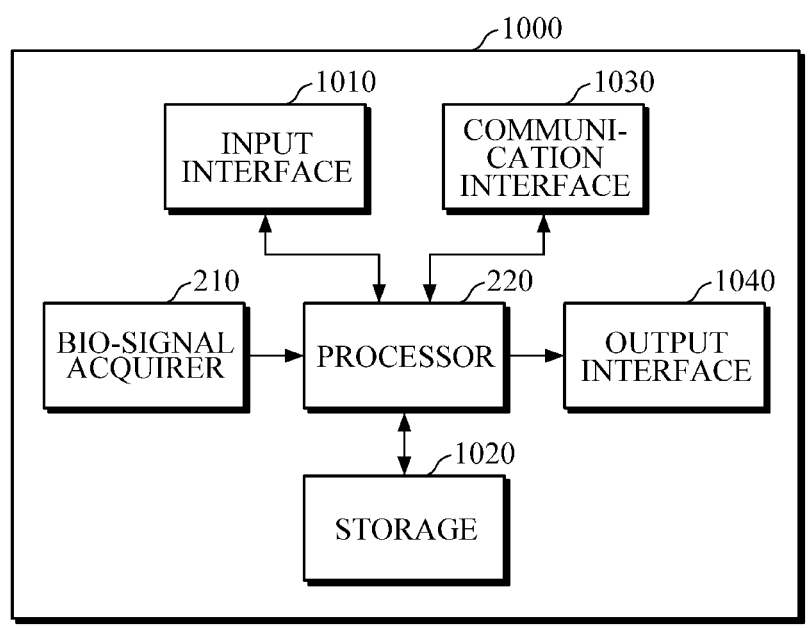
FIG. 10 is a block diagram illustrating an apparatus for detecting a bio-signal feature according to another exemplary embodiment.

FIG. 10 is a block diagram illustrating an apparatus for detecting a bio-signal feature according to another exemplary embodiment.

Referring to FIG. 10, an apparatus 1000 for detecting a bio-signal feature includes a bio-signal acquirer 210, a processor 220, an input interface 1010, a storage 1020, a communication interface 1030, and an output interface 1040. In this case, the bio-signal acquirer 210 and the processor 220 have been described with reference to FIG. 2, and thus detailed descriptions thereof will be omitted.

The input interface 1010 may receive various operation signals input by a user. According to one exemplary embodiment, the input interface 1010 may include a key pad, a dome switch, a capacitive or resistive touch pad, a jog wheel, a jog switch, a hardware button, and the like. In particular, when the touch pad has a layered structure with a display, this structure may be referred to as a touch screen.

The storage 1020 may store programs or instructions for operations of the apparatus 1000 for detecting a bio-signal feature and store data input to the apparatus 1000 and data output from the apparatus 1000. In addition, the storage 1020 may store bio-signal data acquired through the bio-signal acquirer 210 and feature data detected by the processor 220.

The storage 1020 may include at least one type of storage medium, such as a flash memory, a hard disk, a micro type multimedia card, and a card type memory (e.g., secure digital (SD) or XD memory), a random access memory (RAM), a static random access memory (SRAM), a read only memory (ROM), an electrically erasable programmable read only memory (EEPROM), a programmable read only memory (PROM), a magnetic memory, a magnetic disk, and an optical disk. In addition, the apparatus 1000 may operate an external storage medium, such as a web storage serving a storage function.

The communication interface 1030 may communicate with an external device. For example, the communication interface 1030 may transmit the bio-signal data acquired through the bio-signal acquirer 210 and the feature data detected by the processor 220 to the external device and receive various pieces of data helpful for detecting a feature of the bio-signal from the external device.

In this case, the external device may be a medical device using the acquired bio-signal data and/or the bio-signal feature data, a printer to output results, or a display device to display the bio-signal data and the bio-signal feature data. In addition, the external device may be a digital TV, a desktop computer, a mobile phone, a smart phone, a tablet computer, a notebook computer, a PDA, a PMP, a navigation system, an MP3 player, a digital camera, a wearable device, or the like, but is not limited thereto.

The communication interface 1030 may communicate with the external device via Bluetooth communication, Bluetooth low energy (BLE) communication, near-field communication (NFC), wireless local area network (WLAN) communication, ZigBee communication, infrared data association (IrDA) communication, Wi-Fi direct (WFD) communication, ultra-wideband (UWB) communication, Ant+ communication, Wi-Fi communication, radio frequency identification (RFID) communication, 3G communication, 4G communication, 5G communication, or the like. However, these are merely examples and the type of communication is not limited thereto.

The output interface 1040 may output the bio-signal data and/or the bio-signal feature data. According to one exemplary embodiment, the output interface 1040 may output the bio-signal data and/or the bio-signal feature data using at least one of an audible method, a visual method, and a tactile method. To this end, the output interface 1040 may include a display, a speaker, a vibrator, and the like.

Figure 11:
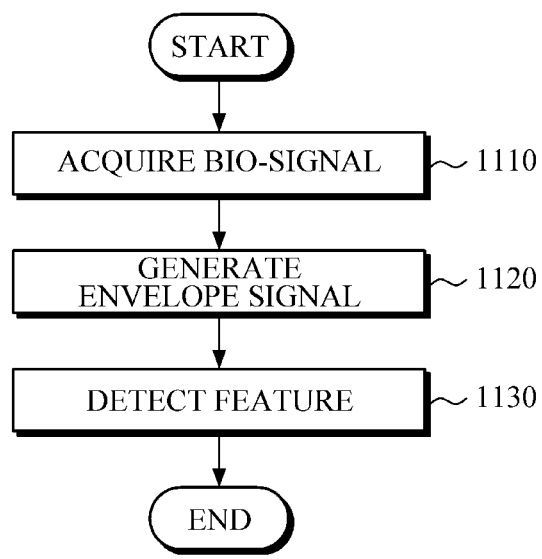
FIG. 11 is a flowchart illustrating a method of detecting a bio-signal feature according to one exemplary embodiment.

FIG. 11 is a flowchart illustrating a method of detecting a bio-signal feature according to one exemplary embodiment. The method shown in FIG. 11 may be performed by the apparatus 200 for detecting a bio-signal feature of FIG. 2.

Referring to FIGS. 2 and 11, the apparatus 200 for detecting a bio-signal feature acquires a bio-signal of one period, in operation 1110. In this case, the bio-signal may be a pulse wave signal (e.g., a PPG signal or a pressure pulse wave signal) a first-order differential signal of a pulse wave signal, or a second-order differential signal of a pulse wave signal. For example, the apparatus 200 may acquire the bio-signal from an external device configured to sense and/or store the bio-signal or may directly acquire the bio-signal using various sensors, such as a PPG sensor, configured to sense the bio-signal.

The apparatus 200 may generate an envelope signal of the bio-signal from the acquired bio-signal, in operation 1120. In this case, the envelope signal may be classified into an upper envelope signal generated based on a peak point of the bio-signal and a lower envelope signal generated based on a valley point of the bio-signal.

The apparatus 200 may detect a feature of the bio-signal using a difference between the generated envelope signal and the bio-signal, in operation 1130. In this case, the feature may be defined as a point that represents a reflection wave component (e.g., the reflection wave components 120 and 130 of FIG. 1) constituting the bio-signal.

Figure 12:
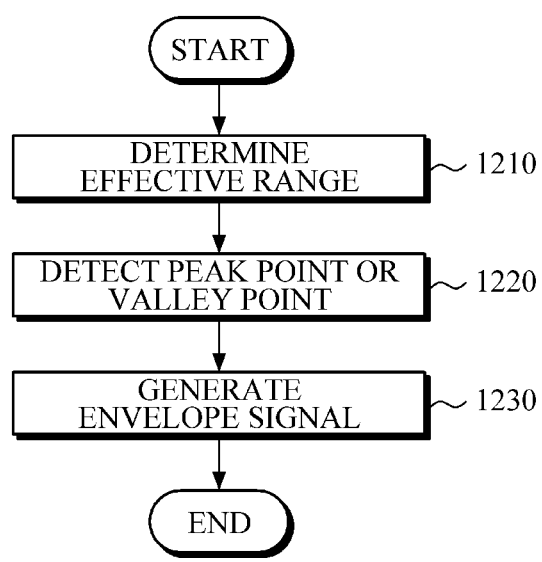
FIG. 12 is a flowchart illustrating an operation of generating an envelope signal of a bio-signal according to one exemplary embodiment.

FIG. 12 is a flowchart illustrating an operation 1120 of generating an envelope signal of a bio-signal according to one exemplary embodiment.

Referring to FIGS. 2 and 12, the apparatus 200 for detecting a bio-signal feature may determine an effective range of the bio-signal, in operation 1210. For example, the apparatus 200 may detect a minimum point and the last zero crossing point or the last valley point of the bio-signal, and determine that a range from the minimum point to the last zero crossing point or the last valley point as the effective range of the bio-signal.

The apparatus 200 may detect at least one peak point or at least one valley point within the effective range of the bio-signal, in operation 1220.

The apparatus 200 may generate an envelope signal of the bio-signal based on the detected at least one peak point and/or the detected at least one valley point, in operation 1230. For example, the apparatus 200 may generate an upper envelope signal by connecting a start point of the effective range, the detected at least one peak point, and an end point of the effective range, or may generate a lower envelope signal by connecting the start point of the effective range, the detected at least one valley point, and the end point of the effective range.

Figure 13:
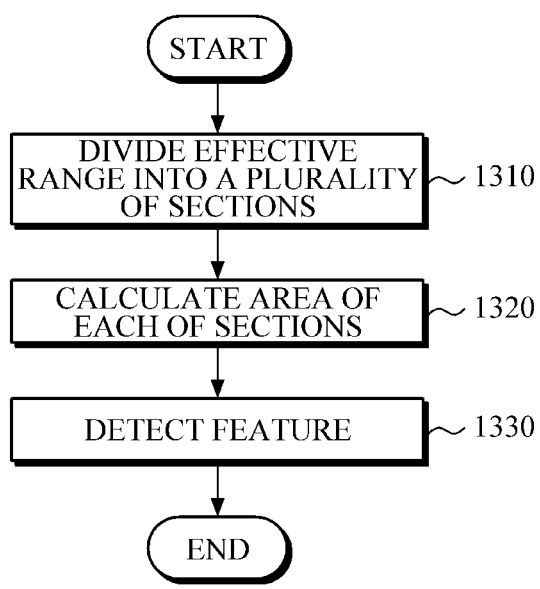
FIG. 13 is a flowchart illustrating an operation of detecting a feature according to one exemplary embodiment.

FIG. 13 is a flowchart illustrating an operation 1130 of detecting a feature according to one exemplary embodiment.

Referring to FIGS. 2 and 13, the apparatus 200 for detecting a bio-signal feature may divide an effective range into a plurality of sections based on the peak point or the valley point within the effective range, in operation 13010. For example, the apparatus 200 may divide the effective range into a plurality of sections based on the peak point within the effective range (when using an upper envelope signal), divide the effective range into a plurality of sections based on the valley point within the effective range (when using a lower envelope signal), or may divide the effective range into a plurality of sections based on the peak point within the effective range and also divide the effective range into a plurality of sections based on the valley point within the effective range (when using both the upper envelope signal and the lower envelope signal).

The apparatus 200 may calculate a difference between the bio-signal and the envelope signal, and calculate an area of each of the sections by summing the differences between the bio-signal and the envelope signal in each section, in operation 1320. For example, the apparatus 200 may calculate a difference between the upper envelope signal and the bio-signal by subtracting the bio-signal from the upper envelope signal and calculate an area of each of the sections by adding absolute values of the differences between the upper envelope signal and the bio-signal in each section (when using the upper envelope signal). In addition, the apparatus 200 may calculate a difference between the bio-signal and the lower envelope signal by subtracting the lower envelope signal from the bio-signal and calculate an area of each of the sections by adding absolute values of the differences between the bio-signal and the lower envelope signal in each section (when using the lower envelope signal). Also, the apparatus 200 may calculate an area of each peak-based section by summing absolute values of differences between the upper envelope signal and the bio-signal in each peak-based section, calculate an area of each valley-based section by summing absolute values of differences between the bio-signal and the lower envelope signal in each valley-based section, and calculate an area of each integrated section by applying a first weight to the area of each peak-based section, applying a second weight to the area of each valley-based section, and thereafter, summing areas of the mutually corresponding sections (when using both the upper envelope signal and the lower envelope signal).

In this case, the apparatus 200 may correct the difference between the upper envelope signal and the bio-signal and the difference between the bio-signal and the lower envelope signal using a scaling function.

The apparatus 200 may select a maximum area section based on the calculated areas for each section and detect a peak point and/or a valley point of the selected maximum area section as a feature of the bio-signal, in operation 1330. For example, the apparatus 200 may select a maximum area section from the plurality of peak-based sections and detect a start point (peak point) of the selected maximum area section and/or a valley point thereof as a feature of the bio-signal (when using the upper envelope signal). In addition, the apparatus 200 may select a maximum area section from the plurality of valley-based sections and detect a peak point of the selected maximum area section and/or an end point (valley point) thereof as a feature of the bio-signal (when using the lower envelope signal). Also, the apparatus 200 may select a maximum integrated area section from a plurality of peak-based sections or from a plurality of valley-based sections and detect a peak point and/or a valley point of the extracted maximum integrated area section as a feature of the bio-signal.

Figure 14:
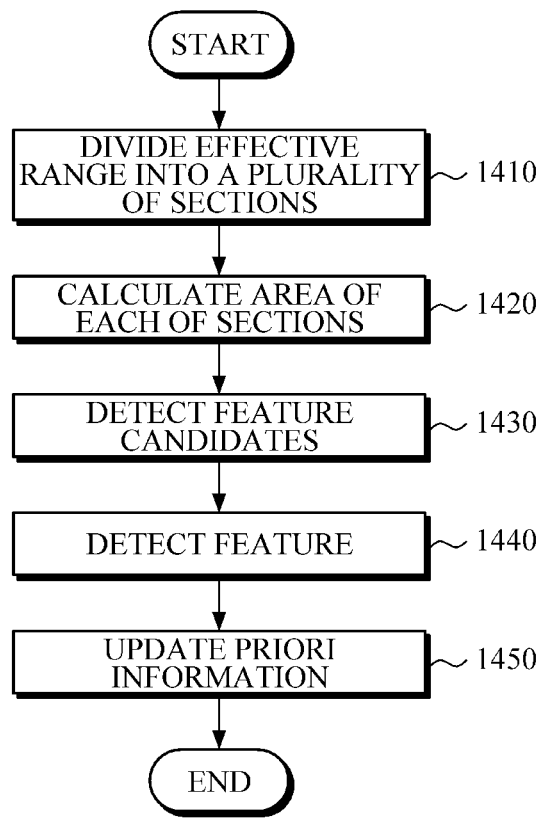
FIG. 14 is a flowchart illustrating the operation of detecting a feature according to another exemplary embodiment.

FIG. 14 is a flowchart illustrating an operation 1130 of detecting a feature according to another exemplary embodiment.

Referring to FIGS. 2 and 14, the apparatus 200 for detecting a bio-signal feature may divide an effective range into a plurality of sections based on a peak point or a valley point within the effective range, in operation 1410.

The apparatus 200 may calculate a difference between the bio-signal and an envelope signal and calculate an area of each of the sections by summing absolute values of the differences between the bio-signal and the envelope signal in each section, in operation 1420.

In this case, the apparatus 200 may correct the difference between the upper envelope signal and the bio-signal and the difference between the bio-signal and the lower envelope signal using a scaling function.

The apparatus 200 may select the top N sections (N is an arbitrary natural number) having large areas based on calculated areas of each section, and detect peak points and/or valley points in the selected N sections as feature candidates, in operation 1440.

The apparatus 200 may detect one of the feature candidates as a feature based on pre-stored priori information, in operation 1440. In this case, the priori information may be information about a position from which the feature is detected. For example, the apparatus 200 may calculate distances between the priori information and each of the feature candidates, and detect the feature candidate that is closest to the priori information as a feature of the bio-signal.

The apparatus 200 may update pre-stored priori information based on position information of the detected feature, in operation 1450.

Meanwhile, the detected features may be used to estimate a blood pressure of the subject from which the bio-signal is measured. For example, various characteristic values (e.g., time, amplitude, etc.) of the bio-signal may be calculated using the features detected by the apparatus 200 for detecting a bio-signal feature and it is possible to estimate the blood pressure of the subject using the various calculated characteristic values and a pre-stored blood pressure estimation equation.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of detecting a bio-signal feature, the method comprising:
   acquiring a bio-signal;
   setting a start point and an end point of an effective range of the bio-signal to a minimum point of the bio-signal, and a last zero crossing point or a last valley point of the bio-signal, respectively;
   obtaining an upper envelope signal by linearly connecting the start point, one or more peak points between the start point and the end point, and the end point of the effective range;
   obtaining a lower envelope signal by linearly connecting the start point, one or more valley points between the start point and the end point, and the end point of the effective range;
   detecting a first feature and a second feature of the bio-signal from a first area formed between the upper envelope signal and the bio-signal and a second area formed between the lower envelope signal and the bio-signal, respectively, based on priori information including at least one feature position;
   estimating a blood pressure based on the first feature and the second feature of the bio-signal;
   updating the priori information based on the first feature or the second feature; and
   providing the estimated blood pressure through a display.

2. The method of claim 1, wherein the bio-signal is a pulse wave signal, a first-order differential signal of the pulse wave signal, or a second-order differential signal of the pulse wave signal.

3. The method of claim 2, wherein the pulse wave signal comprises a photoplethysmogram (PPG) signal and a pressure pulse wave signal.

4. The method of claim 1, wherein the first feature or the second feature represents a reflection wave component constituting the bio-signal.

5. The method of claim 1, wherein the first area is a largest area among a plurality of first sections that are formed between the upper envelope signal and the bio-signal, and the second area is a largest area among a plurality of second sections that are formed between the lower envelope signal and the bio-signal.

6. The method of claim 1, further comprising: applying a scaling function to the first area and the second area.

7. The method of claim 6, wherein the scaling function is generated based on a probability that the feature or the second feature exists in the bio-signal.

8. The method of claim 1, further comprising performing signal smoothing on the bio-signal, so that the upper envelope signal and the lower envelope signal are generated based on the bio-signal, on which the signal smoothing is performed.

9. The method of claim 1, wherein the detecting the first feature and the second feature comprises:
   dividing an effective range of the bio-signal into a plurality of sections;
   determining an area of each of the plurality of sections by summing absolute values of differences between each of the upper envelope signal and the lower envelope signal and the bio-signal in each of the plurality of sections;

detecting at least one of peak points and valley points of largest N sections, among the plurality of sections, as candidate features, wherein N is a natural number; and detecting the first feature and the second feature from the candidate features based on the priori information.

10. The method of claim 9, wherein the detecting the first feature comprises detecting one of the candidate features that is closest to the priori information as the first feature.

* * * * *